(12) United States Patent
Campitelli

(10) Patent No.: US 12,734,315 B2
(45) Date of Patent: Sep. 15, 2026

(54) INHALER ARTICLE HOLDER FOR HIGH DOSE DELIVERY

(71) Applicant: Philip Morris Products S.A., Neuchâtel (CH)

(72) Inventor: Gennaro Campitelli, Neuchâtel (CH)

(73) Assignee: Philip Morris Products S.A., Neuchâtel (CH)

( * ) Notice: Subject to any disclaimer, the term of this patent is extended or adjusted under 35 U.S.C. 154(b) by 536 days.

(21) Appl. No.: 18/281,807

(22) PCT Filed: Mar. 15, 2022

(86) PCT No.: PCT/IB2022/052332
§ 371 (c)(1),
(2) Date: Sep. 13, 2023

(87) PCT Pub. No.: WO2022/195480
PCT Pub. Date: Sep. 22, 2022

(65) Prior Publication Data

US 2024/0157067 A1 May 16, 2024

(30) Foreign Application Priority Data

Mar. 16, 2021 (EP) .................................... 21162955

(51) Int. Cl.
*A61M 15/00* (2006.01)

(52) U.S. Cl.
CPC ...... *A61M 15/0035* (2014.02); *A61M 15/004* (2014.02); *A61M 2202/064* (2013.01); *A61M 2206/16* (2013.01)

(58) Field of Classification Search
CPC ............ A61M 15/0035; A61M 15/004; A61M 2206/16; A61M 2206/064
See application file for complete search history.

(56) References Cited

U.S. PATENT DOCUMENTS 3,918,451 A * 11/1975 Steil .................. A61M 15/0028 128/203.21
5,366,122 A * 11/1994 Guentert ............... A61M 13/00 128/200.22
11,338,099 B2 * 5/2022 Zuber ............... A61M 15/0008
(Continued)

FOREIGN PATENT DOCUMENTS

EP 3393560 B1 3/2020
WO WO-2004091705 A1 * 10/2004 ........ A61M 15/0028
(Continued)

OTHER PUBLICATIONS

European Search Report for EP 21162955.5 issued by the European Patent Office on Sep. 9, 2021; 11 pgs.
(Continued)

*Primary Examiner* — Joseph D. Boecker
*Assistant Examiner* — Thomas W Greig
(74) *Attorney, Agent, or Firm* — Mueting Raasch Group

(57) ABSTRACT

An inhaler article holder is configured to induce swirling inhalation airflow to an inhaler article. The holder is configured to cooperate with the inhaler article to deliver a high dose of dry powder to the user over a limited number of inhalation. The holder and an inhaler article may form an inhaler system to which this disclosure is also directed.

20 Claims, 5 Drawing Sheets

(56) References Cited

U.S. PATENT DOCUMENTS

| | | | | |
|---|---|---|---|---|
| 2003/0150453 | A1* | 8/2003 | Edwards | A61M 15/0028 128/203.21 |
| 2011/0120463 | A1* | 5/2011 | Esteve | A61M 15/0035 128/203.15 |
| 2011/0220106 | A1* | 9/2011 | Ganem | A61M 15/0028 128/203.21 |
| 2018/0043111 | A1* | 2/2018 | Ahern | A61M 15/003 |
| 2018/0369513 | A1* | 12/2018 | Hannon | A61M 15/0086 |
| 2020/0197637 | A1* | 6/2020 | Buehler | A24F 40/485 |
| 2020/0289769 | A1* | 9/2020 | Poullain | A61M 15/0041 |

FOREIGN PATENT DOCUMENTS

| | | | | |
|---|---|---|---|---|
| WO | WO-2019130158 | A1 * | 7/2019 | A61M 11/003 |
| WO | WO 2020/178714 | A1 | 9/2020 | |
| WO | WO 2021/079345 | A1 | 4/2021 | |

OTHER PUBLICATIONS

International Search Report for PCT/IB2022/052332, issued by the European Patent Office on Jun. 7, 2022; 16 pgs.
Marple et al., "Next Generation Pharmaceutical Impactor (A new Impactor for Pharmaceutical Inhaler Testing). Part I: Design," *Journal of Aerosol Medicine*, 2003;16(3); 283-299.
Marple et al., "Next Generation Pharmaceutical Impactor (A new Impactor for Pharmaceutical Inhaler Testing). Part II: Archival Calibration," *Journal of Aerosol Medicine*, 2003;16(3); 301-324.

* cited by examiner

INHALER ARTICLE HOLDER FOR HIGH DOSE DELIVERY

This application is the § 371 U.S. National Stage of International Application No. PCT/IB2022/052332, filed 15 Mar. 2022, which claims the benefit of European Application No. 21162955.5, filed 16 Mar. 2021, the disclosures of which are incorporated herein by reference.

The present disclosure relates to an inhaler article holder, the inhaler article holder is configured to generate swirling inhalation airflow into an inhaler article received in the inhaler article holder.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts.

Inhaler articles may retain capsules containing dry powder. These capsules may be activated by piercing an aperture though the capsule wall. A user puffs (draws or inhales) from the consumable mouthpiece side. This action forces air flow through the dry powder inhaler. Consumers with compromised lung function may have a difficult time operating these dry powder inhalers or delivering dry powder into their lungs.

It is desirable to provide a holder for an inhaler article that activates the inhaler article, retains the inhaler article during consumption, and delivers a high dose of dry powder to the user over a limited number of inhalations. It would be desirable to provide an inhaler system that includes a low-profile and reusable holder for an inhaler article that can activate the inhaler article. It would be desirable to provide an inhaler article made from recyclable material. It would be desirable to provide a powder inhaler that provides an entire dose of particles to the lungs at inhalation or air flow rates that are within conventional smoking regime inhalation or air flow rates within a limited number of inhalations. It would be desirable to provide an inhaler system for providing dry powder in a few inhalations. It would be desirable to provide an inhaler system for providing dry powder in a single inhalation. It would also be desirable to deliver the powder with an inhaler article that has a form similar to a conventional cigarette.

This disclosure is directed to a holder for an inhaler article. The holder is configured to induce swirling inhalation airflow to an inhaler article during consumption. The holder is configured to cooperate with the inhaler article to deliver a high dose of dry powder to the user over a limited number of inhalation. For example, the holder and inhaler article may deliver the entire dose of dry powder to the user over five or fewer inhalations. The holder and an inhaler article may form an inhaler system to which this disclosure is also directed.

According to an aspect of the present invention, there is provided an inhaler article holder including a housing defining a housing cavity, a sleeve positioned within the housing cavity, and a piercing element positioned within the housing cavity. The sleeve is arranged to receive an inhaler article and is movable within the housing cavity between a first position and a second position along a longitudinal axis of the housing cavity. The sleeve includes a sleeve cavity defined by the sleeve, a first open end configured to receive an inhaler article, and a second end opposing the first open. The first open end may be angled. The second end includes an end wall at least partially closing the second end. A tubular member is fixed to the end wall and extending, a first length, from the end wall to a tubular member open end, into the sleeve cavity. The tubular member defines a tubular member cavity having a tubular member longitudinal axis. At least two air inlets extend into the tubular member cavity. The at least two air inlets extend orthogonally to the tubular member longitudinal axis. The least two air inlets enter the tubular member cavity tangentially to induce a swirled airflow pattern on inhalation air entering the sleeve cavity. The at least two air inlets each enter the tubular member cavity through a sleeve side wall and each of the at least two air inlets have a lateral opening dimension in a range from about 0.2 mm to about 0.5 mm. The at least two air inlets each enter the tubular member cavity through a sleeve side wall and adjacent to the end wall and each of the at least two air inlets have a lateral opening dimension in a range from about 0.2 mm to about 0.5 mm. The piercing element is arranged to pass through the end wall and pierce the inhaler article received within the sleeve when the sleeve is in the second position.

According to another aspect of the present invention, an inhaler system includes an inhaler article and the holder for an inhaler article described herein. The inhaler article includes a body extending along an inhaler longitudinal axis from a mouthpiece end to a distal end, and a capsule disposed within the inhaler article body. The sleeve retains the inhaler article received in the sleeve cavity.

Advantageously, incorporating a swirl generating structure into a reusable holder may simplify the construction of the inhaler articles and reduce the complexity of the inhaler system. The described configuration of the holder may discharge the at least 75%-wt or substantially the entire mass of dry powder contained within a capsule with five or fewer inhalations, or three or fewer inhalations, operating at about five litres/min or less inhalation rate. Inhaler articles that receive swirling inhalation airflow may be easier to manufacture and have a simpler construction than inhaler articles that incorporate structures to induce or form swirling inhalation airflow. The simpler inhaler articles may also present less environmental burden.

The inhaler article holder and inhaler article may be used for the inhalation of any desired dry powder. According to an embodiment, a capsule contained by the inhaler article contains dry powder comprising particles containing one or more pharmaceutically active agents. Examples of pharmaceutically active agents include nicotine, anatabine, hydroxychloroquine, epinephrine, melatonin, caffeine, antiviral compounds such as acyclovir; anti-inflammatory compounds such as salicylic acid, aceclofenac, or ketoprofen; antidiabetic compounds such as metformin or glipizide; antihypertensive compounds such as oxprenolol; antiemetic compounds such as promethazine; antidepressant compounds such as seproxetine; anticoagulant compounds such as picotamide; bronchodilators such as clenbuterol; or anticancer compounds such as beta-lapachone. The capsule may contain any dry powder pharmaceutically active agent.

The pharmaceutically active agent may include a pharmaceutically acceptable salt of the agent. Suitable salts include, for example, a salt of lactic acid ("lactate"), tartaric acid ("tartrate" or "bitartrate"), aspartic acid ("aspartate"), pyruvic acid ("pyruvate"), citric acid ("citrate"), salicylic acid ("salicylate"), glutamic acid ("glutamate"), gentisic acid ("gentisate"), benzoic acid ("benzoate"), fumaric acid ("fumarate"), hydrochloric acid ("hydrochlorate"), alfa-resorcylic acid ("alfa-resorcylate"), beta-resorcylic acid ("beta-resorcylate"), oxalic acid ("oxalate"), p-anisic acid ("anisate"), glutaric acid ("glutarate"), and the like.

The capsule may hold or contain 5 mg or more, or 10 mg or more of dry powder particles. The capsule may hold or contain 900 mg or less, 600 mg or less, 300 mg or less, or 150 mg or less of dry powder particles. The capsule may hold or contain from 5 mg to 300 mg, or from 10 mg to 200 mg, or from 25 mg to 100 mg, or from 30 mg to 75 mg of dry powder particles.

The capsule may contain flavor particles. When flavor particles are blended or combined with the pharmaceutically active particles in the capsule, the flavor particles may be present in an amount that provides the desired flavor to each inhalation or "puff" delivered to the user. The pharmaceutically active particles may make up 40 wt-% or more, 60 wt-% or more, or 80 wt-% or more of the dry powder. The pharmaceutically active particles may make up from 50 wt-% to 90 wt-%, or from 60 wt-% to 85 wt-%, or 70 wt-% to 80 wt-% of the dry powder.

The capsule may be made of any suitable material. For example, the capsule may be made of a polymeric material, gelatin, or any other suitable material for making fillable capsules. In one embodiment, the capsule is made from polymeric material, preferably hydroxypropyl-methylcellulose ("HPMC"). For example, the capsule may be a size 1 HPMC capsule. The capsule may be a size 2 HPMC capsule. The capsule may be a size 3 HPMC capsule. The capsule may be a size 4 HPMC capsule. The capsule may be a size 1 gelatin capsule. The capsule may be a size 2 gelatin capsule. The capsule may be a size 3 gelatin capsule. The capsule may be a size 4 gelatin capsule.

The activated capsule includes only a single aperture for releasing the dry powder from within the capsule. The single aperture may have a lateral dimension opening in a range from about 1.5 mm to about 0.7 mm, or from 1.2 mm to about 0.8 mm.

For example, a size 3 or size 4 capsule activated with a single aperture having a largest lateral dimension opening in a range from 1.2 mm to about 0.8 mm and containing from 40 to 60 grams of dry powder, may release at least 75%-wt or at least 80%-wt of the dry powder from the capsule single aperture in two or less inhalations a flow rate of about 5 litres/min each having a duration of about 2 seconds, utilizing the inhaler system described herein.

The inhaler article holder is configured to cooperate with the inhaler article to deliver a high dose of dry powder to the user over a limited number of inhalation. For example, the holder and inhaler article may deliver substantially the entire dose of dry powder contained within the capsule to the user over five or fewer inhalations. The holder and inhaler article may deliver substantially the entire dose of dry powder contained within the capsule to the user over four or fewer inhalations. The holder and inhaler article may deliver substantially the entire dose of dry powder contained within the capsule to the user over three or fewer inhalations. The holder and inhaler article may deliver substantially the entire dose of dry powder contained within the capsule to the user over two or fewer inhalations. The holder and inhaler article may deliver substantially the entire dose of dry powder contained within the capsule to the user over a single inhalation. "Substantially the entire dose of dry powder" means at least 75%-wt of the total dry powder contained in the capsule.

The inhalations may flow thought the inhaler article at an inhalation flow rate that is within conventional smoking regime inhalation air flow rates. The inhalations may flow thought the inhaler article at an inhalation flow rate less than five litres/min, or in a range from two litres/min to five litres/min, or from three litres/min to five litres/min, or from four litres/min to five litres/min.

Each inhalation may flow thought the inhaler article in a time duration equal to a normal inhalation breath of a user. Each inhalation may flow thought the inhaler article in a time duration in a range from about 1 to 4 seconds. Each inhalation may flow thought the inhaler article a time duration in a range from about 1 to 3 seconds. Each inhalation may flow thought the inhaler article in a time duration in a range from about 1.5 to 2.5 seconds. Each inhalation may flow thought the inhaler article in a time duration of about 2 seconds.

The capsule may contain a pharmaceutically active powder comprising particles with mass median aerodynamic diameter (hereinafter "MMAD") particle size in the range of 0.5 to 10 micrometers, or 0.5 to 5 micrometers. In one embodiment, the capsule contains nicotine powder comprising nicotine particles, where the nicotine particles have MMAD particle size in the range of 0.5 to 10 micrometers, or 0.5 to 5 micrometers. The capsule may further contain flavor particles having MMAD particle size of 10 micrometers or greater, 20 micrometers or greater, or 40 micrometers or greater. The flavor particles may have MMAD particle size of 200 micrometers or less, 150 micrometers or less, or 120 micrometers or less. The flavor particles may have MMAD particle size of 20 micrometers to 200 micrometers or from 40 micrometers to 120 micrometers. In some embodiments, the capsule contains nicotine particles having MMAD particle size in the range of 0.5 micrometers to 10 micrometers, or 0.5 micrometers to 5 micrometers and flavor particles having MMAD particle size of 20 micrometers to 200 micrometers or from 50 micrometers to 150 micrometers.

In some cases, the capsule contains pharmaceutically active particles comprising nicotine. For example, the capsule may contain a dry powder comprising nicotine salt. The dry powder may further contain other components, such as sugar or sugar alcohol, amino acid, flavorant, cough suppressant, or other pharmaceutically acceptable ingredients that are suitable for use in inhalable powders. In one embodiment, the capsule contains nicotine powder comprising nicotine particles, where the nicotine particles comprise nicotine salt, sugar or sugar alcohol, and amino acid. The nicotine powder particles may composite particles where at least selected or each particle includes nicotine salt, sugar or sugar alcohol, and amino acid. The capsule may further comprise flavor particles, cough suppressant particles, or both flavor and cough suppressant particles. Flavor and cough suppressant particles are collectively referred to here as flavor particles.

The nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The nicotine particles preferably include an amino acid. Preferably the amino acid may be leucine such as L-leucine. Providing an amino acid, such as L-leucine, with the particles comprising nicotine may reduce adhesion forces of the particles and may reduce attraction between nicotine particles, thus reducing agglomeration of nicotine particles and adherence of the nicotine particles to surfaces. Similarly, adhesion forces to particles comprising flavor may also be reduced. The powder system may be a free-flowing material and possess a stable relative particle size of each powder component even when the nicotine particles and the flavor particles are combined.

This disclosure is directed to a holder for an inhaler article, referred to as an "inhaler article holder". The inhaler article holder includes one or more piercing elements. The inhaler article holder is configured to receive a consumable inhaler article, activate the capsule within the inhaler article by piercing the capsule, and induce swirling inhalation airflow into an inhaler article during consumption. The inhaler article holder and an inhaler article may form an inhaler system to which this disclosure is directed. The inhaler article holder may include a single piercing element.

The inhaler article holder described herein may be combined with an inhaler article containing a capsule. The inhaler article may be used to activate the inhaler article by piercing the capsule, providing reliable activation of the capsule by puncturing the capsule with the piercing element of the inhaler article holder. Particles may be released from the capsule upon drawing or creating an airflow around the pierced capsule. The inhaler system thus delivers the dry powder particles to a consumer. The inhaler article holder is separate from the inhaler article, but the consumer utilizes both the inhaler article and the inhaler article holder while consuming the dry powder particles released within the inhaler article. A plurality of these inhaler articles may be combined with an inhaler article holder to form a system or kit. A single inhaler article holder may be utilized on 10 or more, or 25 or more, or 50 or more, or 100 or more, inhaler articles to activate (puncture or pierce) a capsule contained within each inhaler article and provide reliable activation. The inhaler article may optionally provide a visual indication (marking), for each inhaler article of the activation of the inhaler article.

An inhaler article comprises an elongated tubular body extending along an inhaler longitudinal axis from a mouthpiece end to a distal end. The mouthpiece end is the proximal end, or the downstream end. The distal end is the upstream end. A capsule cavity is defined within the body bounded downstream by a filter element and bounded upstream by an open tubular element defining a central passage. Prior to insertion into an inhaler article holder, the distal end of the inhaler article may be closed. After insertion into an inhaler article holder, the distal end of the inhaler article may be open. The distal end of the inhaler article may interact with complimentary structures in the inhaler article holder so that, upon introducing the inhaler article into the inhaler article holder, the distal end of the inhaler article may open. When introduced into the inhaler article holder, the distal end of the inhaler article has a central passage which forms an open air-inlet aperture extending from the distal end of the body to the capsule cavity. A capsule is disposed within the capsule cavity, the central passage may have a smaller diameter then the capsule. Thus, the capsule may not pass through the central passage and is retained within the capsule cavity.

The inhaler article has an airflow path. Airflow is introduced into the inhaler article by an inhalation (or puff) from a user. The inhaler article holder creates swirling inhalation airflow. This swirling inhalation airflow is introduced to the inhaler article. The distal end or upstream-most end of the inhaler article includes an open aperture that defines an open central passage of the open tubular element configured to receive swirling inhalation airflow.

The swirling inhalation airflow then continues downstream into the capsule cavity and induces rotation of a capsule in the capsule cavity. The activated capsule then releases a dose of particles into the swirling inhalation airflow downstream through the mouthpiece to the consumer. Thus, the swirling inhalation airflow is created upstream from the inhaler article and swirling inhalation airflow enters the distal end or upstream-most end of the inhaler article.

Applicant has discovered that the number, size, and placement of air inlets into the swirling air generating structure within described the inhaler article holder results in different capsule depletions of dry powder during use. Specifically, the number, size, and placement of air inlets into the swirling air generating structure within the inhaler article holder changes the rate of capsule spinning and capsule shaking frequency. At least 75%-wt of the total dry powder is withdrawn from the capsule within two inhalations (each at a rate of about 4 to about 5 liters/min for about 2 seconds) when three or four air inlets are utilized into the swirling air generating structure where each air inlet has a lateral size or diameter in a range from 0.2 mm to 0.5 mm, or from 0.2 mm to 0.4 mm, or from 0.2 mm to 0.3 mm. Resistance to draw may be in a range from 30 mmWG to about 110 mmWG.

The inhaler article holder includes a housing comprising a housing cavity for receiving an inhaler article and a sleeve configured to retain an inhaler article within the housing cavity. The housing cavity is defined by a single housing opening that extends into the housing to a closed end along a housing longitudinal axis. The single housing opening is configured to receive the inhaler article.

The sleeve is contained within the housing cavity and is movable along the housing longitudinal axis between a first position and a second position. The sleeve may be slidable along the housing longitudinal axis between a first position and a second position. In the first position the sleeve is located adjacent to the single housing opening. In the second position the sleeve is further away from the single housing opening a lateral distance along the longitudinal axis. The sleeve is arranged and configured to receive an inhaler article.

The sleeve extends from a first open end to a second end opposing the first open end and defines a cylindrical lumen or sleeve cavity along a longitudinal axis of the sleeve. The open end of the sleeve aligns with the single housing opening and is configured to receive the inhaler article. The second end includes an end wall at least partially closing the second end. The open end of the sleeve may be angled. This angle may facilitate insertion of the open end of the sleeve into the inhaler article when the inhaler article is introduced into the device. In addition, an angled open end may facilitate manufacture of the sleeve part by facilitating the removal of the part from a plastic mold.

A tubular member is fixed to the end wall and extends a first length, from the end wall to a tubular member open end, into the sleeve cavity. The tubular member defines a tubular member cavity having a tubular member longitudinal axis. The tubular member longitudinal axis preferable is co-axial with the sleeve longitudinal axis.

At least two air inlets extend into the tubular member cavity. The at least two air inlets extend orthogonally to the tubular member longitudinal axis. The least two air inlets enter the tubular member cavity tangentially to induce a swirled airflow pattern on inhalation air entering the sleeve cavity.

The two, three or four air inlets are arranged and configured to dispense at least 75%-wt or at least 80%-wt of the dry powder from the capsule via a capsule single aperture with two or fewer inhalations. The at least two air inlets each enter the tubular member cavity adjacent to the end wall. Each of the at least two air inlets have a lateral opening dimension in a range from about 0.2 mm to about 0.5 mm.

Placing the air inlets closer to the end wall improves the dispensing properties of the inhaler article. Placing the air inlets furthest from the tubular member open end improves the dispensing properties of the inhaler article. The at least two air inlets each enter the tubular member cavity close to the end wall. The tubular member has a first length value from the end wall to the open end. The at least two air inlets enter the tubular member cavity within the first 25% of the first length value from the end wall. The at least two air inlets enter the tubular member cavity within the first 10% of the first length value from the end wall. The at least two air inlets enter the tubular member cavity within the first 5% of the first length value from the end wall. The at least two air inlets enter the tubular member cavity within a distance value to the end wall being less than the lateral opening dimension of each air inlet. The at least two air inlets enter the tubular member cavity at an intersection of the end wall and the tubular member.

At least 75%-wt of the total dry powder is withdrawn from the capsule within two inhalations (each at a rate of about 4 to about 5 liters/min for about 2 seconds) when three air inlets extend into the tubular member cavity. The three air inlets extend orthogonally to the tubular member longitudinal axis. The three air inlets enter the tubular member cavity tangentially to induce a swirled airflow pattern on inhalation air entering the sleeve cavity. The three air inlets each enter the tubular member cavity adjacent to the end wall. Each of the three air inlets has a lateral opening dimension or diameter in a range from 0.25 mm to 0.4 mm, or from 0.27 mm to 0.33 mm, or about 0.3 mm. Resistance to draw may be in a range from 30 mmWG to about 70 mmWG, or from 50 mmWG to about 70 mmWG.

At least 75%-wt of the total dry powder is withdrawn from the capsule within two inhalations (each at a rate of about 4 to about 5 liters/min for about 2 seconds) when four air inlets extend into the tubular member cavity. The four air inlets extend orthogonally to the tubular member longitudinal axis. The four air inlets enter the tubular member cavity tangentially to induce a swirled airflow pattern on inhalation air entering the sleeve cavity. The four air inlets each enter the tubular member cavity adjacent to the end wall. Each of the four air inlets has a lateral opening dimension or diameter in a range from 0.2 mm to 0.3 mm, or from 0.24 mm to 0.3 mm, or about 0.29 mm. Resistance to draw may be in a range from 45 mmWG to about 110 mmWG.

The sleeve end wall includes an aperture to allow the piercing element to pass through the end wall and extend into the sleeve lumen. The air inlets provide airflow communication from the annular space around the sleeve into the sleeve cylindrical lumen. The air inlets and tubular member are configured to induce rotating or swirling inhalation airflow into the sleeve cylindrical lumen and directly into the inhaler article capsule cavity. This swirling or rotational inhalation airflow may be transmitted into an inhaler article to rotate a capsule and release dry powder contained within the capsule.

The inhaler article holder may include a piercing element fixed to and extending from a housing inner surface of the cavity. The piercing element is configured to extend through the end wall of the sleeve and into the sleeve cavity along a longitudinal axis of the housing. The piercing element contacts and pierces the capsule of a received inhaler article once the sleeve moves from the first position to the second position. Moving the sleeve from the second position to the first position removes the piercing element from the capsule and exposes an aperture in the capsule that allows dry particles contained within the capsule to be released from the capsule as inhalation air rotates the capsule.

The inhaler article holder may further include a spring member configured to bias the sleeve away from the piercing element. The spring member may bias the sleeve away from the second position to the first position. The spring member may be in a relaxed state in the sleeve first position. The spring member may be in a compressed state in the second position. Preferably the piercing element is disposed within the spring member.

The sleeve may include an elongated slot extending along a longitudinal length of the sleeve. The housing may further include a pin extending from an inner surface of the housing cavity. The pin may be configured to mate with the elongated slot to maintain alignment of the sleeve as it moved between the first and second positions.

An inner housing may be contained within the housing cavity. The inner housing may separate at least a portion of the sleeve from the inner surface of the housing cavity. The inner housing may separate a fixed end of the piercing element from the inner surface of the housing cavity. The inner housing may separate at the spring member from the inner surface of the housing cavity.

The tubular element may extend into the sleeve cavity and may form an annular recess with the sleeve cavity configured to receive a distal end of an inhaler article. The tubular element may extend into the sleeve cavity and forms an annular recess with the sleeve cavity configured to retain a distal end of an inhaler article. The tubular element may be configured to extend into a distal end of an inhaler article received within the sleeve cavity. Substantially all of the inhalation air enters the tubular element in a direction that is tangential to the tubular member longitudinal axis.

Advantageously, providing features on the second opposing end of the sleeve that mate with a received inhaler article may improve the reliable airflow connection from the swirl inducing sleeve to the inhaler article received in the sleeve. The annular recess may be configured to retain the distal end of an inhaler article with an interference fit. An interference fit between the annular recess and the distal end of the inhaler may also provide a secure engagement of the inhaler article received in the sleeve so that the inhaler article will not fall out of the sleeve or associated holder.

The term "particle size" is used here to refer to the mass median aerodynamic diameter (MMAD) of the particle or set of particles, unless otherwise stated. Such values are based on the distribution of the aerodynamic particle diameters defined as the diameter of a sphere with a density of 1 gm/$cm^3$ that has the same aerodynamic behavior as the particle which is being characterized.

In particular for a powder system reference is commonly made to the mass median aerodynamic diameter (MMAD), one of the metrics most widely adopted as a single number descriptor of aerodynamic particle-size distribution. The MMAD is a statistically derived figure for a particle sample: by way of example, an MMAD of 5 micrometres means that 50 percent of the total sample mass will be present in particles having aerodynamic diameters of less than 5 micrometres, and that the remaining 50 percent of the total sample mass will be present in particles having an aerodynamic diameter greater than 5 micrometres. In the context of the present invention, when describing a powder system, the term "particle size" preferably refers to the MMAD of the powder system.

The MMAD of a powder system is preferably measured with a cascade impactor. Cascade impactors are instruments which have been extensively used for sampling and separating airborne particles for determining the aerodynamic size classification of aerosol particles. In practice, cascade impactors separate an incoming sample into discrete fractions on the basis of particle inertia, which is a function of particle size, density and velocity. A cascade impactor typically comprises a series of stages, each of which comprises a plate with a specific nozzle arrangement and a collection surface. As nozzle size and total nozzle area both decrease with increasing stage number, the velocity of the sample-laden air increases as it proceeds through the instrument. At each stage, particles with sufficient inertia break free from the prevailing air stream to impact on the collection surface. Therefore, at any given flow rate, each stage is associated with a cut-off diameter, a figure that defines the size of particles collected. With increasing stage number, velocity increases and so stage cut-off diameter decreases. Thus, the cut-off diameter associated with a given stage is a function of the air-flow rate used for testing. To reflect in-use performance, nebulisers are routinely tested at 15 L/min and dry powder inhalers may be tested at flow rates up to 100 L/min.

Preferably, in the context of the present invention, the MMAD of a powder system is measured with a Next Generation Impactor (NGI) 170 (available from Copley Scientific AG). The NGI is a high performance, precision, particle classifying cascade impactor having seven stages plus a Micro-Orifice Collector (MOC). Characteristics and operation principle of a NGI are described, for example, in Marple et al., Journal of Aerosol Medicine—Volume 16, Number 3 (2003). More preferably, measurements are carried out at 20±3 degrees Celsius and relative humidity of 35±5 percent.

A dry powder formulation typically contains less than or equal to about 15 percent by weight moisture, preferably less than or equal to about 10 percent moisture, even more preferably less than or equal to about 6 percent by weight moisture. Most preferably a dry powder formulation contains less than or equal to about 5 percent by weight moisture or even less than or equal to about 3 percent by weight moisture or even less than or equal to about 1 percent by weight moisture.

The phrase "resistance to draw" or "RTD", refers to the static pressure difference between the two ends of a specimen when it is traversed by an air flow under steady conditions in which the volumetric flow is 17.5 millilitres per second at the output end. The RTD of a specimen can be measured using the method set out in ISO Standard 6565:2002.

All values reported as a percentage are presumed to be weight percent based on the total weight.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

The term "substantially" as used here has the same meaning as "significantly," and can be understood to modify the relevant term by at least about 90%, at least about 95%, or at least about 98%. The term "not substantially" as used here has the same meaning as "not significantly," and can be understood to have the inverse meaning of "substantially," i.e., modifying the relevant term by not more than 10%, not more than 5%, or not more than 2%.

The terms "upstream" and "downstream" refer to relative positions of elements of the holder, inhaler article and inhaler systems described in relation to the direction of inhalation air flow as it is drawn through the body of the holder, inhaler article and inhaler systems.

The invention is defined in the claims. However, below there is provided a non-exhaustive listing of non-limiting examples. Any one or more of the features of these examples may be combined with any one or more features of another example, embodiment, or aspect described herein.

Example Ex1. An inhaler article holder comprising, including a housing defining a housing cavity, a sleeve positioned within the housing cavity, and a piercing element positioned within the housing cavity. The sleeve is arranged to receive an inhaler article and is movable within the housing cavity between a first position and a second position along a longitudinal axis of the housing cavity. The sleeve includes a sleeve cavity defined by the sleeve, a first open end configured to receive an inhaler article, and a second end opposing the first open. The second end includes an end wall at least partially closing the second end. A tubular member is fixed to the end wall and extending, a first length, from the end wall to a tubular member open end, into the sleeve cavity. The tubular member defines a tubular member cavity having a tubular member longitudinal axis. At least two air inlets extend into the tubular member cavity. The at least two air inlets extend orthogonally to the tubular member longitudinal axis. The least two air inlets enter the tubular member cavity tangentially to induce a swirled airflow pattern on inhalation air entering the sleeve cavity. The at least two air inlets each enter the tubular member cavity adjacent to the end wall and each of the at least two air inlets have a lateral opening dimension in a range from about 0.2 mm to about 0.5 mm. The piercing element is arranged to pass through the end wall and pierce the inhaler article received within the sleeve when the sleeve is in the second position.

Example Ex2. The inhaler article holder of Ex1, wherein the tubular member includes three air inlets extending into the tubular member cavity. The three air inlets extend orthogonally to the tubular member longitudinal axis. The three air inlets enter the tubular member cavity tangentially to induce a swirled airflow pattern on inhalation air entering the sleeve cavity. The three air inlets each enter the tubular member cavity adjacent to the end wall.

Example Ex3. The inhaler article holder of Ex2, wherein each of the three air inlets have a lateral opening dimension in a range from about 0.25 mm to about 0.4 mm, or in a range from about 0.27 mm to about 0.33 mm, or about 0.3 mm.

Example Ex4. The inhaler article holder of Ex1, wherein the tubular member includes four air inlets extending into the tubular member cavity. The four air inlets extend orthogonally to the tubular member longitudinal axis. The four air inlets enter the tubular member cavity tangentially to induce a swirled airflow pattern on inhalation air entering the sleeve cavity. The four air inlets each enter the tubular member cavity adjacent to the end wall.

Example Ex5. The inhaler article holder of Ex4, wherein each of the four air inlets have a lateral opening dimension in a range from about 0.2 mm to about 0.3 mm, or in a range from about 0.24 mm to about 0.3 mm, or about 0.29 mm.

Example Ex6. The inhaler article holder of Ex2 or Ex3, wherein a resistance to draw is in a range of about 30 mmWG to about 70 mmWG, about 50 mmWG to about 70 mmWG.

Example Ex7. The inhaler article holder of Ex4 or Ex5, wherein a resistance to draw is in a range of about 45 mmWG to about 110 mmWG.

Example Ex8. The inhaler article holder of any preceding Example, wherein the air inlets each enter the tubular member cavity within a distance value to the end wall being less than the lateral opening dimension of the air inlet.

Example Ex9. The inhaler article holder of any preceding Example, wherein the air inlets each enter the tubular member cavity at an intersection of the end wall and the tubular member.

Example Ex10. The inhaler article holder of any preceding Example, wherein the tubular member extends into the sleeve cavity and forms an annular recess with the sleeve cavity configured to receive a distal end of an inhaler article.

Example Ex11. The inhaler article holder of any preceding Example, wherein the tubular member is coaxial with a longitudinal axis of the sleeve.

Example Ex12. An inhaler system comprising, an inhaler article and the holder for an inhaler article according to any preceding Example. The inhaler article includes a body extending along an inhaler longitudinal axis from a mouthpiece end to a distal end, and a capsule disposed within the inhaler article body. The sleeve retains the inhaler article received in the sleeve cavity.

Example Ex13. The inhaler article system of Ex12, wherein the capsule is retained within a capsule cavity and configured to receive swirling inhalation airflow formed by the second end of the sleeve, the capsule cavity is bounded downstream by a porous element and bounded upstream by an open tubular element.

Example Ex14. The inhaler system of Ex12 or Ex13, wherein the capsule contains pharmaceutically active particles. The pharmaceutically active particles have a mass median aerodynamic diameter of about 5 micrometres or less, or in a range from about 0.5 micrometres to about 4 micrometres, or in a range from about 1 micrometres to about 3 micrometres.

Example Ex15. The inhaler system of Ex12 to Ex14, wherein the tubular member and the sleeve form an annular recess, and the distal end of the inhaler article mates with the annular recess.

Example Ex16. The inhaler system of Ex 10 or Ex. 15 wherein the open end of the sleeve is angled.

The Examples will now be further described with reference to the figures in which.

Figure 1:
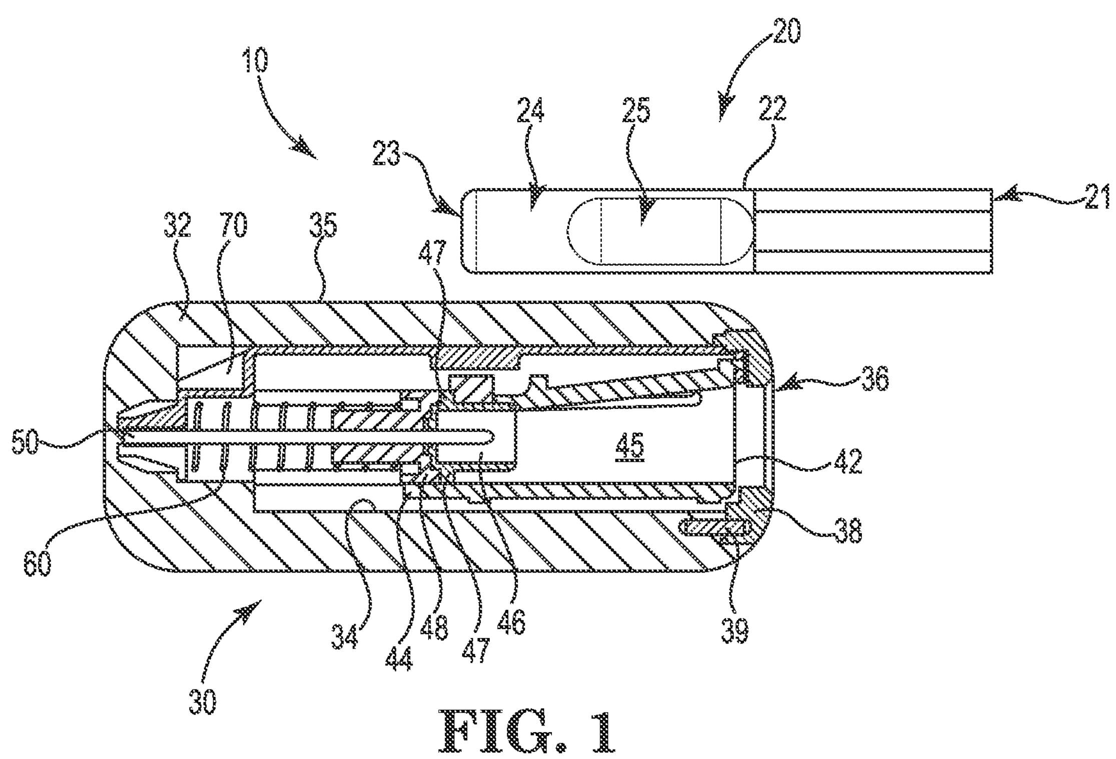
FIG. 1 is a schematic cross-sectional diagram of an illustrative inhaler system.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 2:
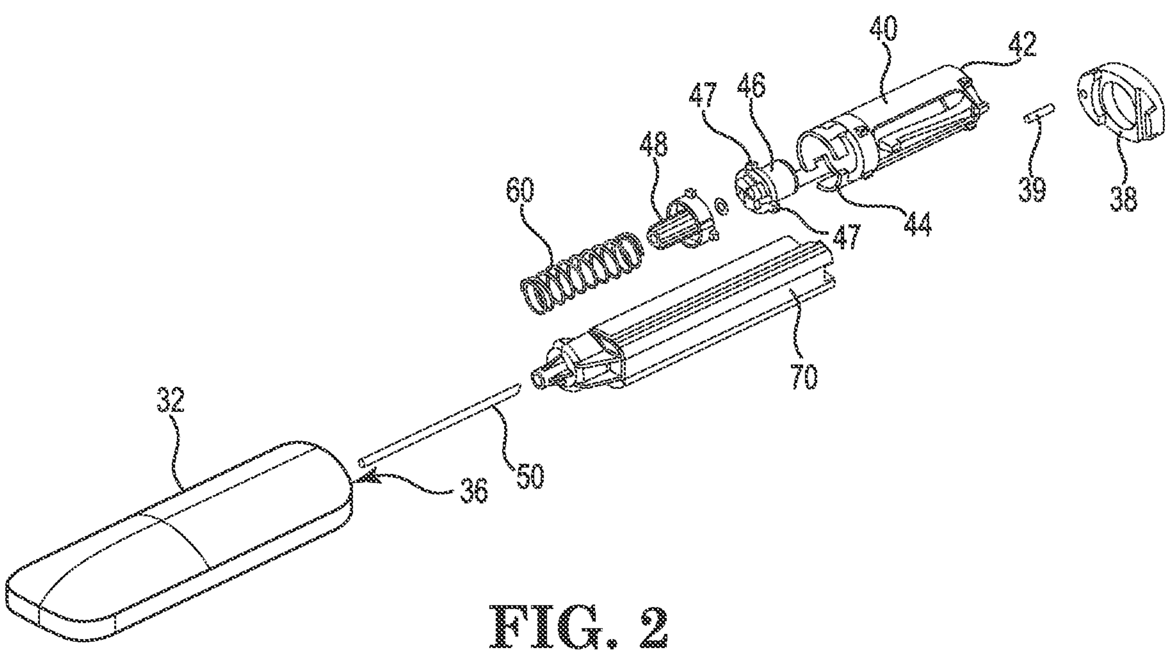
FIG. 2 is perspective exploded view of an illustrative inhaler article holder.
Figure 3A:
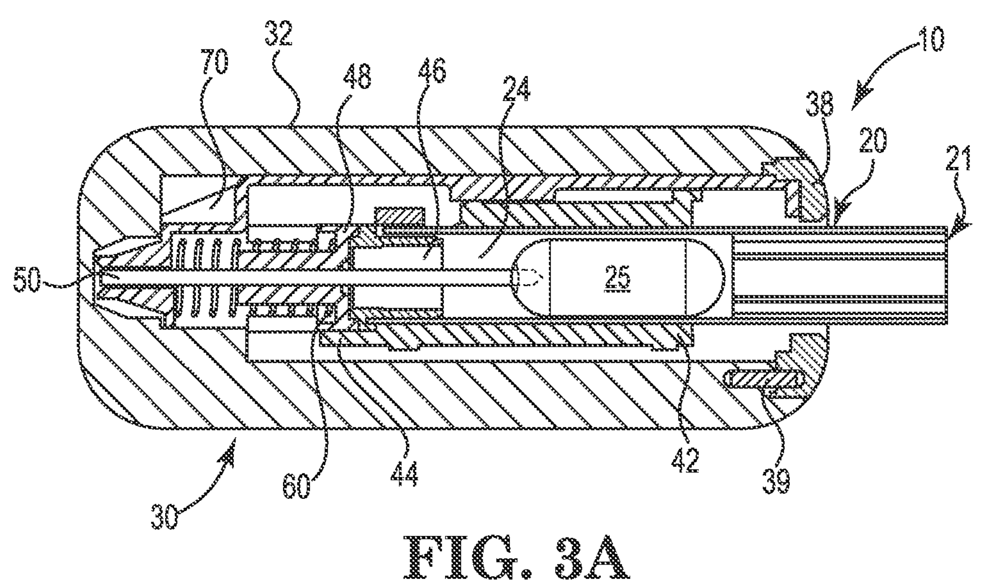
FIG. 3A is a schematic cross-sectional diagram of an illustrative inhaler system where the inhaler article is received in the inhaler article holder and piercing the capsule in a second position.
Figure 3B:
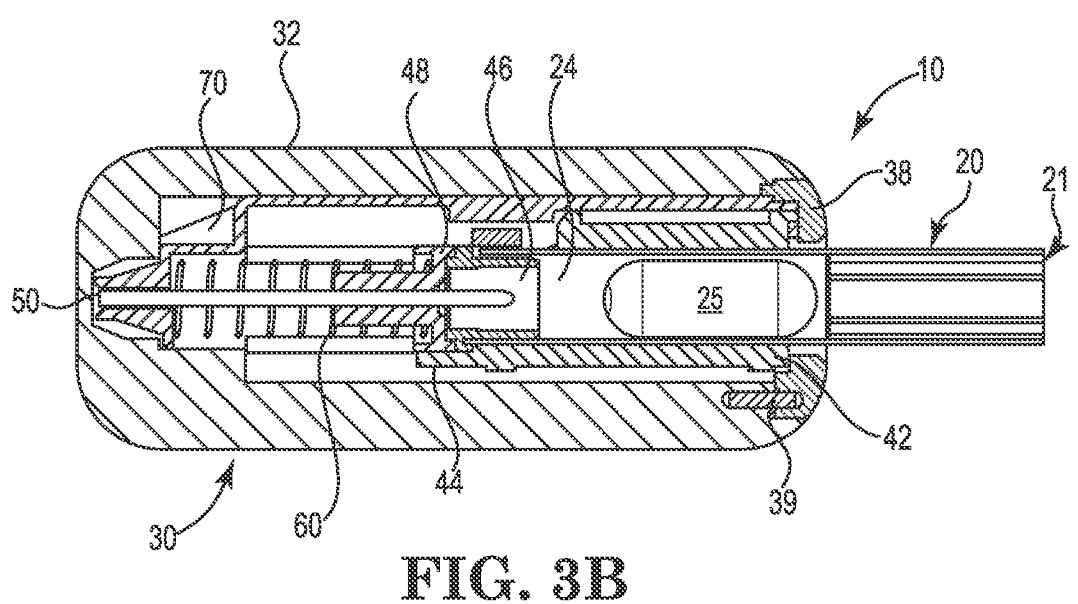
FIG. 3B is a schematic cross-sectional diagram of the illustrative inhaler system of FIG. 3A where the piercing element is retracted from the capsule in a first position.
Figure 4:
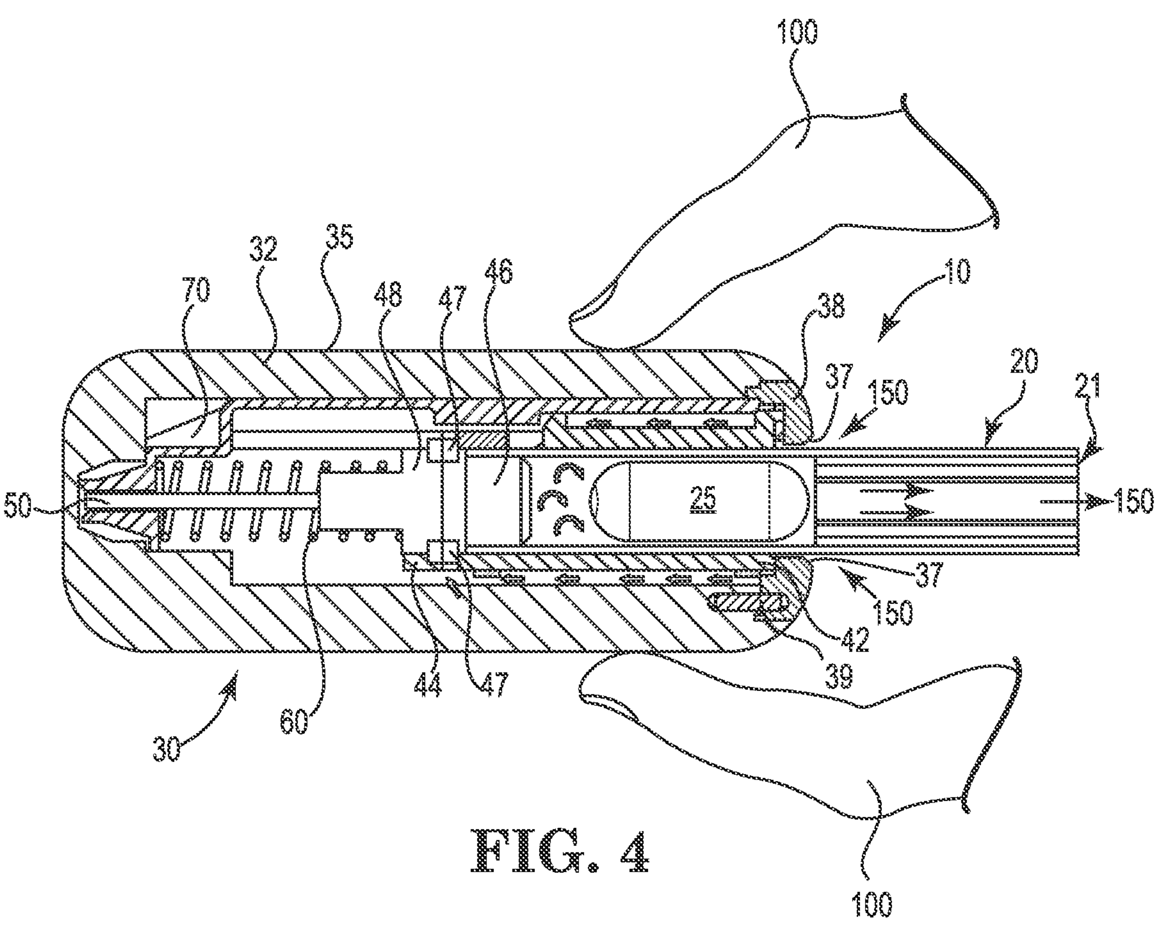
FIG. 4 is another schematic cross-sectional diagram of FIG. 3B illustrating the inhalation airflow path through the inhaler system.

FIG. 1 is a schematic cross-sectional diagram of an illustrative inhaler system 10. FIG. 2 is perspective exploded view of an illustrative inhaler article holder 30. FIG. 3A is a schematic cross-sectional diagram of an illustrative inhaler system 10 where the inhaler article 20 is received in the inhaler article holder 30 and the capsule 25 is pierced by the piercing element 50 when the inhaler article holder 30 is in a second or compressed position. FIG. 3B is a schematic cross-sectional diagram of the illustrative inhaler system 10 of FIG. 3A where the piercing element 50 is retracted from the capsule 25 in a first or relaxed position. FIG. 4 is another schematic cross-sectional diagram of FIG. 3B illustrating the inhalation airflow 150 path (arrows) through the inhaler system 10.

The inhaler article holder 30 is configured to receive a separate consumable inhaler article 20 and induce swirling inhalation airflow into and through an inhaler article 20 during consumption. The inhaler article holder 30 and an inhaler article 20 form an inhaler system 10. The inhaler article 20 remains in the inhaler article holder 30 during use by the consumer. The inhaler article holder 30 is configured to induce swirling inhalation airflow entering the received inhaler article 20.

The illustrative inhaler article 20 includes a body 22 extending from a mouthpiece end 21 to a distal end 23. A capsule cavity 24 is defined within the body 22. A capsule 25 is contained within the capsule cavity 24. Dry powder particles described above may be contained within the capsule 25. The capsule 25 may be pierced to form an aperture through the body of the capsule 25 and inhalation air may flow through the inhaler article 20 to release dry powder particles from the pierced capsule 25 and into the inhalation airflow and out of the mouthpiece end 21.

The inhaler article holder 30 includes a housing 32 defining a housing cavity defined by a housing inner surface 34, and an outer surface 35. A sleeve 40 is positioned within the housing cavity. The sleeve 40 is arranged to receive an inhaler article 20 and the sleeve 40 is movable within the housing cavity between a first position (FIG. 3B) and a second position (FIG. 3A), along a longitudinal axis of the housing cavity.

A piercing element 50 is arranged to pierce the capsule 25 within the inhaler article 20 received within the sleeve 40 when the sleeve 40 is in the second position as illustrated in FIG. 3A. The piercing element 50 may be configured to extend into the sleeve 40 along a longitudinal axis of the housing 32. The inhaler article holder 30 may include a spring member 60 configured to bias the sleeve 40 and any received inhaler article 20 away from the piercing element 50.

The sleeve 40 extends from a first open end 42 to an opposing second end 44 and defines a sleeve cavity 45 defines a cylindrical lumen along a longitudinal axis of the sleeve 40. The sleeve cavity 45 may optionally have ridges or other structures inside the lumen to assist with holding the inhaler article 20 in place during use. The first open end 42 of the sleeve aligns with the single housing opening 36. The second end 44 includes an end wall 48 at least partially closing the second end. The end wall 48 includes an aperture to allow the piercing element 50 to pass through the end wall 48 and extend into the sleeve 40 cavity.

A tubular member 46 is fixed to the end wall 48 and extends from the end wall 48 into the sleeve 40 cavity a first length. The tubular member 46 defining a tubular member cavity having a tubular member longitudinal axis. The first length may be about 5 mm. The tubular member 46 may have an outer diameter of about 5.5 mm and an inner diameter of about 4 mm. The received inhaler article 20 open distal end 23 may have an inner diameter of about 5.5 mm to provide an interference fit with the tubular member 46.

At least two air inlets 47 extend into the tubular member 46 cavity. The at least two air inlets 47 extend orthogonally to the tubular member longitudinal axis. The least two air inlets 47 enter the tubular member 46 cavity tangentially to induce a swirled airflow pattern on inhalation air entering the sleeve 40 cavity. The at least two air inlets 47 each enter the tubular member 46 cavity through the sidewall of the sleeve 40. The at least two air inlets 47 may each enter the tubular member 46 cavity adjacent to the end wall 48. Each of the at least two air inlets 47 have a lateral opening dimension in a range from about 0.2 mm to about 0.5 mm.

The tubular member 46 includes two or more inhalation air inlets 47 that provide airflow communication from the annular space around the sleeve 40 into the sleeve cavity 45. This tubular member 46 is configured to induce rotating or swirling inhalation airflow into the sleeve cavity 45 and directly into the inhaler article capsule cavity 24. This swirling or rotational inhalation airflow may be transmitted into an inhaler article 20 to rotate a capsule 25 and release dry powder contained within the capsule 25.

An inner housing 70 may be contained within the housing cavity. The inner housing 70 may separate at least a portion of the sleeve 40 from the inner surface of the housing cavity. The inner housing 70 may separate a fixed end of the piercing element 50 from the inner surface of the housing cavity. The inner housing 70 may separate the spring member 60 from the inner surface of the housing cavity.

An annular cover 38 may secure the inner housing 70 and sleeve 40 into the housing cavity. The annular cover 38 defines the single housing opening 36 for receiving the inhaler article 20. The annular cover 38 may be fixed to the housing 32 with a pin element 39.

FIG. 4 illustrates the inhalation airflow 150 path through the inhaler system 10. Inhalation airflow 150 is introduced into the device by the inhalation of a user. Inhalation air 150 enters the inhaler article holder 30 between the outer surface of the received inhaler article 20 and the annular cover 38 defining an inhalation inlet 37. This inhalation inlet 37 into the device may define an annular opening coaxial with the received inhaler article 20.

Once inside the housing cavity, the inhalation air 150 travels along the sleeve 40 length to the second end 44 of the sleeve 40. The inhalation air 150 then enters the air inlets 47 of the tubular member 46 and forms swirling or rotating inhalation airflow 150 within the sleeve cavity 45. This swirling or rotating inhalation air is then directly transmitted into the distal end 23 of the inhaler article 20 and into the capsule cavity 24. The swirling inhalation airflow rotates or agitates the capsule 25 and dry powder particles are entrained in the inhalation airflow. The entrained inhalation airflow then flows out of the inhaler article via the mouthpiece end 21 and to the user 100. The inhalation airflow 150 path is illustrated in FIG. 4 with arrows.

Figure 5:
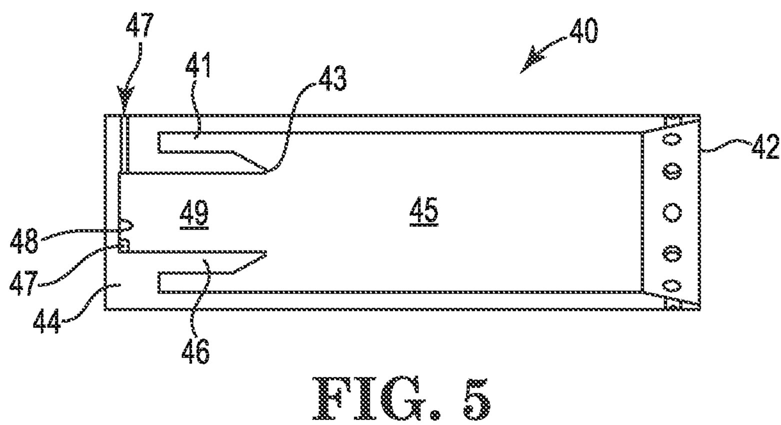
FIG. 5 is a cross-sectional schematic diagram of an illustrative sleeve.
Figure 6:
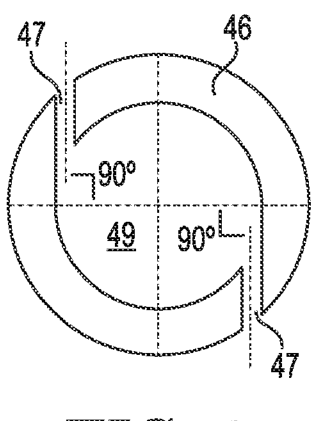
FIGS. 6-8 are cross-sectional schematic diagrams of illustrative tubular members with one to four tangential air inlets.
Figure 7:
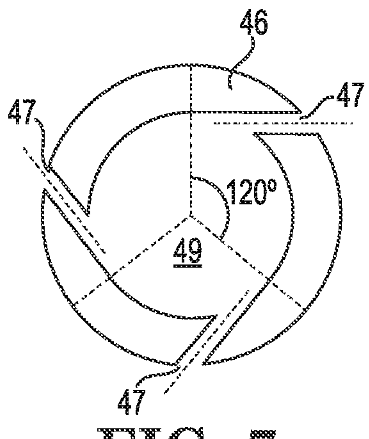
Figure 8:
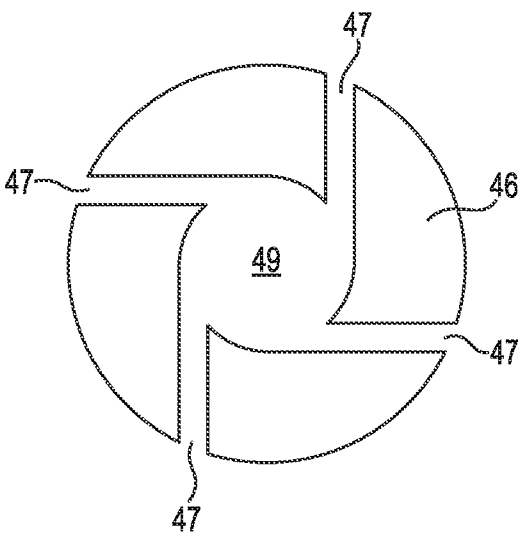

FIG. 5 is a cross-sectional schematic diagram of an illustrative sleeve 40. FIGS. 6-8 are cross-sectional schematic diagrams of illustrative tubular members 46 with two to four tangential air inlets 47.

The sleeve 40 extends from a first open end 42 to an opposing second end 44 and defining a sleeve cavity 45. The second end 44 includes an end wall 48 at least partially closing the second end 44.

The second end 44 of the sleeve 40 includes a tubular member 46 defining a tubular member cavity 49. The tubular member 46 extend from the end wall 48 to an open end 43. The open end 43 may be angled. This angle may facilitate insertion of the tubular member 46 into the inhaler article 20 when the inhaler article 20 is introduced into the device. The tubular member cavity 49 is in fluid communication with the sleeve cavity 45. The tubular member 46 open end 43 extends into the sleeve cavity 45. The tubular member 46 includes at least two air inlets 47 allowing air to enter into tubular member cavity 49. The at least two air inlets 47 extend in a direction that is tangential to the tubular member cavity 49.

The tubular member cavity 49 may extend a longitudinally from the end wall 48 to an open end 43 defining a length having a distance of about 5 mm. The at least two air inlets 47 may enter the tubular member cavity 49 within the first 2 mm (first 40%) of the length of the tubular member cavity 49 from the end wall 48. The at least two air inlets 47 may enter the tubular member cavity 49 within the first 1.5 mm (first 30%) of the length of the tubular member cavity 49 from the end wall 48. The at least two air inlets 47 may enter the tubular member cavity 49 within the first 1 mm (first 20%) of the length of the tubular member cavity 49 from the end wall 48. The at least two air inlets 47 may enter the tubular member cavity 49 within the first 0.5 mm (first 10%) of the length of the tubular member cavity 49 from the end wall 48.

The distal end 23 of the inhaler article 20 slides onto the tubular member 46. Inhalation air inlets 47 enter the tubular member 46 at a tangent to the tubular member cavity 49 and form swirling inhalation airflow to the received inhaler article 20. The tubular member 46 extends into the sleeve cavity 45 and forms an annular recess 41 with the sleeve cavity 45 configured to receive a distal end 23 of an inhaler article 20. The projection formed by the tubular member 46 slides into the inhaler article 20 open distal end 23. The tubular member 46 is configured to extend into a distal end 23 of an inhaler article 20 received within the sleeve cavity 45.

FIGS. 6-9 are cross-sectional schematic diagrams of illustrative tubular members 46 with tubular member cavity 49 with two to four tangential air inlets 47. The inner diameter of the tubular members 46 is about 4 mm. FIG. 6 illustrates two tangential air inlets 47 each having a diameter or lateral opening dimension of about 0.4 mm to about 0.5 mm entering the tubular member 46 at 180 degrees from each other. FIG. 7 illustrates three tangential air inlets 47 each having a diameter or lateral opening dimension of about 0.3 mm to about 0.4 mm entering the tubular member 46 at 120 degrees from each other. FIG. 8 illustrates four tangential air inlets 47 each having a diameter or lateral opening dimension of about 0.25 mm to about 0.3 mm entering the tubular member 46 at 90 degrees from each other.

EXAMPLES

Inhalation tests were performed on the inhaler systems described herein. All the tests utilized an inhaler article having a size 3 capsule containing 50 mg of nicotine salt powder and flavor particles (75% nicotine salt:25% Flavor particles weight ratio). The nicotine salt particles had a MMAD of about 1-3 micrometers. The flavor particles had a MMAD of about 50-100 micrometers. The capsules were activated with a 1.2 mm diameter piercing element to form a single aperture in the capsule. Each test provided inhalation airflow through the inhaler system at 75 ml/s for about 2 second for each inhalation.

An inhaler system having three air inlets as illustrated in FIG. 7 was tested having a diameter or lateral opening dimension of 0.36 mm (Example A) and 0.30 mm (Example B) entering the tubular member at 120 degrees from each other.

Example A had a RTD of about 35 mmWG and released about 75%-wt of the total dry powder dose from the capsule after two inhalations.

Example B had a RTD of about 60 mmWG and released about 80%-wt of the total dry powder dose from the capsule after two inhalations.

An inhaler system having four air inlets as illustrated in FIG. 8 was tested having a diameter or lateral opening dimension of 0.3 mm (Example C) and 0.25 mm (Example D) entering the tubular member at 120 degrees from each other.

Example C had a RTD of about 50 mmWG and released about 75%-wt of the total dry powder dose from the capsule after two inhalations.

Example D had a RTD of about 100 mmWG and released about 75%-wt of the total dry powder dose from the capsule after two inhalations.

Applicant discovered that these results were realized once the air inlets were located close to the end wall of the tubular member.

For comparison, Applicant tested the inhaler system having three air inlets as illustrated in FIG. 7 was tested having a diameter or lateral opening dimension of 0.85 mm (Example C1) entering the tubular member at 120 degrees from each other. Here the test provided inhalation airflow through the inhaler system at 40 ml/s for about 2 second for each inhalation.

Comparative Example C1 had an RTD of about 35 mmWG and delivered a lower dose of powder for each inhalation that was generally uniform for 12-20 inhalations to achieve release of about 75%-wt of the total dry powder dose from the capsule.

For the purpose of the present description and of the appended claims, except where otherwise indicated, all numbers expressing amounts, quantities, percentages, and so forth, are to be understood as being modified in all instances by the term "about." Also, all ranges include the maximum and minimum points disclosed and include any intermediate ranges therein, which may or may not be specifically enumerated herein. In this context, therefore, a number A is understood as A ±2% of A. Within this context, a number A may be considered to include numerical values that are within general standard error for the measurement of the property that the number A modifies. The number A, in some instances as used in the appended claims, may deviate by the percentages enumerated above provided that the amount by which A deviates does not materially affect the basic and novel characteristic(s) of the claimed invention. Also, all ranges include the maximum and minimum points disclosed and include any intermediate ranges therein, which may or may not be specifically enumerated herein.

The invention claimed is:

1. An inhaler article holder comprising:

a housing defining a housing cavity;

a sleeve positioned within the housing cavity, the sleeve is arranged to receive an inhaler article, the inhaler article comprising a body extending along an inhaler longitudinal axis from a mouthpiece end to an inhaler article open distal end and a capsule disposed within the inhaler article body, the sleeve is movable within the housing cavity between a first position and a second position along a longitudinal axis of the housing cavity, the sleeve comprises:

a sleeve cavity defined by the sleeve;

a first open end configured to receive an inhaler article;

a second end opposing the first open end, the second end comprises an end wall at least partially closing the second end;

a tubular member fixed to the end wall and extending, a first length from the end wall to a tubular member open end, into the sleeve cavity, the tubular member defining a tubular member cavity having a tubular member longitudinal axis, the tubular member configured to slide into the inhaler article open distal end; and at least two air inlets extend into the tubular member cavity, the at least two air inlets extend orthogonally to the tubular member longitudinal axis, the at least two air inlets enter the tubular member cavity tangentially to induce a swirled airflow pattern on inhalation air entering the sleeve cavity, the at least two air inlets each enter the tubular member cavity adjacent to the end wall and each of the at least two air inlets have a lateral opening dimension in a range from about 0.2 mm to about 0.5 mm;

a spring member configured to bias the sleeve away from the second position to the first position; and a piercing element arranged to pass through the end wall and pierce the inhaler article received within the sleeve when the sleeve is in the second position.

2. The inhaler article holder according to claim 1, wherein the tubular member includes three air inlets extending into the tubular member cavity, the three air inlets extend orthogonally to the tubular member longitudinal axis, the three air inlets enter the tubular member cavity tangentially to induce a swirled airflow pattern on inhalation air entering the sleeve cavity, the three air inlets each enter the tubular member cavity adjacent to the end wall.

3. The inhaler article holder according to claim 2, wherein each of the three air inlets have a lateral opening dimension in a range from about 0.25 mm to about 0.4 mm.

4. The inhaler article holder according to claim 1, wherein the tubular member includes four air inlets extending into the tubular member cavity, the four air inlets extend orthogonally to the tubular member longitudinal axis, the four air inlets enter the tubular member cavity tangentially to induce a swirled airflow pattern on inhalation air entering the sleeve cavity, the four air inlets each enter the tubular member cavity adjacent to the end wall.

5. The inhaler article holder according to claim 4, wherein each of the four air inlets have a lateral opening dimension in a range from about 0.2 mm to about 0.3 mm.

6. The inhaler article holder according to claim 2, wherein a resistance to draw is in a range of about 30 mmWG to about 70 mmWG.

7. The inhaler article holder according to claim 4, wherein a resistance to draw is in a range of about 45 mmWG to about 110 mmWG.

8. The inhaler article holder according to claim 1, wherein the air inlets each enter the tubular member cavity within a distance value to the end wall being less than the lateral opening dimension of the air inlet.

9. The inhaler article holder according to claim 1, wherein the air inlets each enter the tubular member cavity at an intersection of the end wall and the tubular member.

10. The inhaler article holder according to claim 1, wherein the tubular member extends into the sleeve cavity and forms an annular recess with the sleeve cavity configured to receive a distal end of an inhaler article.

11. The inhaler article holder according to claim 1, wherein the tubular member is coaxial with a longitudinal axis of the sleeve.

12. An inhaler system comprising:

an inhaler article comprising a body extending along an inhaler longitudinal axis from a mouthpiece end to a distal end, and a capsule disposed within the inhaler article body; and the inhaler article holder according to claim 1, wherein the sleeve retains the inhaler article received in the sleeve cavity.

13. The inhaler system according to claim 12, wherein the capsule is retained within a capsule cavity and configured to receive swirling inhalation airflow formed by the second end of the sleeve, the capsule cavity is bounded downstream by a porous element and bounded upstream by an open tubular element.

14. The inhaler system according to claim 12, wherein the capsule contains pharmaceutically active particles, the pharmaceutically active particles having a mass median aerodynamic diameter in a range from about 0.5 micrometres to about 4 micrometres.

15. The inhaler system according to claim 12, wherein the tubular member and the sleeve form an annular recess, and the distal end of the inhaler article mates with the annular recess.

16. The inhaler article holder according to claim 2, wherein each of the three air inlets have a lateral opening dimension in a range from 0.27 mm to 0.33 mm.

17. The inhaler article holder according to claim 4, wherein each of the four air inlets have a lateral opening dimension in a range from 0.24 mm to about 0.3 mm.

18. The inhaler article holder according to claim 16, wherein a resistance to draw is in a range of about 50 mmWG to about 70 mmWG.

19. The inhaler system according to claim 13, wherein the tubular member and the sleeve form an annular recess, and the distal end of the inhaler article mates with the annular recess.

20. The inhaler system according to claim 19, wherein the capsule contains pharmaceutically active particles, the pharmaceutically active particles having a mass median aerodynamic diameter in a range from about 0.5 micrometres to about 4 micrometres.

* * * * *